United States Patent [19]

Mozayeni

[11] Patent Number: 5,434,079
[45] Date of Patent: Jul. 18, 1995

[54] APPARATUS AND PROCESS FOR CONTINUOUS IN VITRO SYNTHESIS OF PROTEINS

[75] Inventor: Bobak R. Mozayeni, Rockville, Md.

[73] Assignee: The United States of America as represented by the Department of Health and Human Services, Washington, D.C.

[21] Appl. No.: 17,062

[22] Filed: Feb. 12, 1993

[51] Int. Cl.$^6$ .................................... B01D 63/08
[52] U.S. Cl. ............................... 435/311; 435/291; 210/321.75; 935/88
[58] Field of Search ................ 435/291, 311; 935/85–88; 210/644, 456, 247, 321.75, 321.84

[56] References Cited

U.S. PATENT DOCUMENTS

| | | | |
|---|---|---|---|
| 736,745 | 8/1903 | Kubin | 210/321.75 |
| 3,074,559 | 1/1963 | Savino | 210/321.75 |
| 4,956,085 | 9/1990 | Kopf | 210/456 |

OTHER PUBLICATIONS

Kvist et al., "A Nucleoprotein Peptide Of Influence A Virus Stimulates Assembly Of HLA-B27 Class 1 Heavy Chains And $\beta_2$-micro-blobulin Translated *in vitro*", *Nature*, vol. 348:446–448, (1990).
Parker et al., "Peptide Binding To HLA-A2 And HLA-B27 Isolated From Eschericha Coli", *The Journal Of Biological Chemistry*, vol. 267:5451–5459, (1992).
Matsumura et al., "In Vitro Peptide Binding To Soluble Empty Class I Major Histocompatibility complex Molecules Isolated From Transfected Drosophila Melanogaster Cells", *The Journal Of Biological Chemistry*, vol. 267:23589–23595, (1992).
W. Scouten, "Immobilized Cell Free Translation Systems", *National Institute Of General Medical Sciences*, 1992), Abstract.
Spirin et al., "A continuous Cell-Free Translation System Capable Of Producing Polypeptides in High Yield", *Science*, vol. 242:1162–1164, (1988).
Ryabova et al., "Preparative Synthesis Of Globin In A Continuous Cell-Free Translation System From Rabbit Reticulocytes", *Nucleic Acids Research*, vol. 17:4412, (1989).
Baranov et al., "Gene Expression In A Cell-Free System On the Preparative Scale", *Gene*, vol. 84:463–466, (1989).
Kigawa et al., "A Continuous Cell-Free Protein Synthesis System For Coupled Transcription-Translation", *J. Biochem.*, vol. 110:166–168, (1991).
"A Self-Contained Laboratory Tangential Flow Device For 100ml—2 liter Volumes".
Spirin, "Ribosome Preparation And Cell-Free Protein Synthesis", *Institute of Protein Research*, pp. 56–70, (1990).
Broker et al., "The Electron Micrograph Of Bacteriophage $\gamma$ Particle Stained With Uranyl Acetate Was Digitized And Assigned False Color By Computer", *Molecular Cloning*, pp. 10.30–10.37 and 18.81–18.84, (1989).

*Primary Examiner*—James C. Housel
*Assistant Examiner*—Rachel Heather Freed
*Attorney, Agent, or Firm*—Foley and Lardner

[57] ABSTRACT

An apparatus and process for continuous, cell-free, in vitro synthesis of peptides, particularly peptide-MHC complexes make use of a novel bioreactor flow cell which allows for the reproducible, systematic variation of single parameters in order to optimize translation processes. The bioreactor flow cell includes a pair of substantially parallel membranes positioned within a chamber to define therebetween a space, the ratio of total membrane surface area to chamber volume being at least 5 units$^{-1}$, which permits high perfusion rates through the system with lower flux rate per membrane area. The apparatus also may include a novel countercurrent flow dialysis cell and other components.

23 Claims, 3 Drawing Sheets

APPARATUS AND PROCESS FOR CONTINUOUS IN VITRO SYNTHESIS OF PROTEINS

BACKGROUND OF THE INVENTION

The present invention relates to an apparatus and to a process for continuous, cell-free, in vitro synthesis of proteins and polypeptides, particularly peptide-MHC complexes.

In vivo expression of foreign or synthetic genes, and overexpression of native genes by cells, are subject to a number of limitations. Many gene products are insoluble or unstable and either are degraded by intracellular proteases or aggregate in inclusion bodies. Other products are toxic to the cell and cannot be expressed at all. Several regulatory proteins are unstable, and gene regulation mechanisms can also lead to poor levels of expression.

In vitro expression of proteins in a cell-free system avoids these and other problems. The absence of cellular control mechanisms and the ability to manipulate incubation mixture composition are advantages of this type of system. But low polypeptide yield has been a major obstacle with these systems. Early attempts to express polypeptides in cell-free systems typically produced only two to three polypeptide chains per mRNA chain used.

More recently, Spirin et al. have described a continuous cell-free translation system for producing polypeptides in higher yields. Science 242:1162–1163 (1988); see also Ryabova et al., Nucleic Acids Research 17:4412 (1989), and Baranov et al., Gene 84:463–466 (1989). The Spirin system uses an Amicon 8 MC micro-ultrafiltration device as a bioreactor for polypeptide synthesis. The device is a cylindrical flow cell with a 25 mm diameter membrane mounted at the bottom of the cell. The surface area of this membrane that is available for filtration is about 4 cm$^2$ somewhat less than the 5 cm$^2$ calculated based on its 25 mm diameter because of the O-ring used to mount the membrane in the device. A stirring bar is used to mix feed buffer and lysate contained in the cell.

Spirin's group has reported translation rates for globin of as much as 2 mg from 0.5 ml of rabbit reticulocyte lysate after 100 hours. See Ryabova et al., loc. cit. The volume of this liquid in the flow cell varies during operation, however, between about 1 and 5 ml, due to the compressibility of air in the chamber. The maximum flow rate possible is about 3 ml/hr and this flow rate cannot be maintained during continued operation, but tapers to 2 or even 1 ml/hr over the ensuing 4 to 5 hours. Thus, neither flow rate nor flow cell volume can be maintained during operation.

In addition to difficulties associated with controlling the flow rate and the volume of liquid contained in the flow cell, it also is impossible to control temperature and outgassing in this flow cell. Single parameters therefore cannot be varied systematically in this system. This means that optimization of a process for synthesis of a particular polypeptide is virtually impossible with this type of system.

A purported improvement of the Spirin system is described by Kigawa et al., in which the Amicon 8MC micro-ultrafiltration units was replaced with a reaction chamber with a capacity equal to the reaction mixture volume and in which a high performance liquid chromatography pump was used to supply the substrate solution. J. Biochem. 110:166–168 (1991). This system provided laboratory-scale polypeptide production, with only 0.1 mg of chloramphenicol acetyltransferase being synthesized in 17 hours from 1 ml of reaction mixture.

SUMMARY OF THE INVENTION

It is therefore an object of the present invention to provide an in vitro system for continuous cell-free synthesis of proteins on a preparative scale.

It is a further object of the invention to provide an in vitro system for continuous cell-free synthesis of a polypeptide in which single parameters can be varied systematically, permitting process optimization with respect to a given protein.

It is yet another object of the invention to provide a bioreactor flow cell that does not clog during operation.

It is a further object of the invention to provide a countercurrent flow dialysis cell.

It is another object of the invention to provide a method for continuous, cell-free in vitro synthesis of proteins generally and peptide-MHC complexes in particular.

In accomplishing these and other objects, there has been provided, in accordance with one aspect of the present invention, a bioreactor flow cell comprising a chamber; a pair of substantially parallel membranes positioned within the chamber to define therebetween a space, wherein the ratio of total surface area for the membranes to the volume of the chamber is at least 5 units$^{-1}$; an inlet at one end of the chamber for admitting a solution into the space between the membranes and an outlet at the other end of the chamber for removing the solution from the space between the membranes; means associated with at least one of the inlet and the outlet for attaching at least one sensor to monitor a property of a solution flowing through the bioreactor flow cell; and an eluate port in communication with the chamber.

Also provided, according to another aspect of the present invention, is a bioreactor flow cell comprising a chamber; a pair of substantially parallel membranes positioned within the chamber to define therebetween a space, wherein the ratio of total surface area for the membranes to the volume of the chamber is at least 5 units$^{-1}$; an inlet at one end of the chamber for admitting a solution into the space between the membranes and an outlet at the other end of the chamber for removing the solution from the space between the membranes; thermal transfer means associated with at least one of the inlet and the outlet for affecting the temperature of a solution flowing into the bioreactor flow cell; and an eluate port in communication with the chamber.

A further aspect of the present invention relates to a countercurrent flow dialysis cell comprising an upper housing having on its inner surface a grooved pattern with an inlet and an outlet, a lower housing having on its inner surface a grooved pattern with an inlet and an outlet, and a dialysis membrane positioned between the upper and lower housings, wherein the lower housing grooved pattern is a mirror image of the upper housing grooved pattern, with the inlet of the upper housing grooved pattern being adjacent the outlet of the lower housing grooved pattern and the outlet of the upper housing grooved pattern being adjacent the inlet of the lower housing grooved pattern.

An in vitro system for continuous cell-free synthesis of a protein on a preparative scale is also provided which comprises a bioreactor cell according to the invention and means for circulating a feed buffer containing amino acids and an mRNA construct encoding a protein through the bioreactor cell. The system may additionally include a countercurrent flow dialysis cell and other components.

A method for continuous, cell-free in vitro synthesis of a polypeptide is provided that comprises steps of introducing a mixture of a cell lysate and a feed buffer containing an mRNA construct encoding a protein into a system according to the present invention, circulating the mixture through the bioreactor flow cell, and eluting protein encoded by the mRNA construct through the membranes of the bioreactor cell.

Also provided is a method for continuous, cell-free in vitro synthesis of peptide-MHC complexes, comprising the steps of chemically synthesizing a peptide; adding the peptide to a feed buffer that contains amino acids to produce a feed mixture; introducing a cell lysate and an mRNA construct which encodes a MHC molecule and the feed mixture into a system according to the present invention, forming a reaction mixture; circulating the reaction mixture through the bioreactor flow cell; and eluting peptide-MHC protein complex through the membranes of the bioreactor cell.

Other features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIGS. 2A, 2B and 2C show a preferred embodiment of a bioreactor flow cell according to the present invention.

FIGS. 3A, 3B and 3C show a preferred embodiment of a countercurrent flow dialysis cell according to the present invention.

DETAILED DESCRIPTION OF PREFERRED EMBODIMENTS

Figure 1:
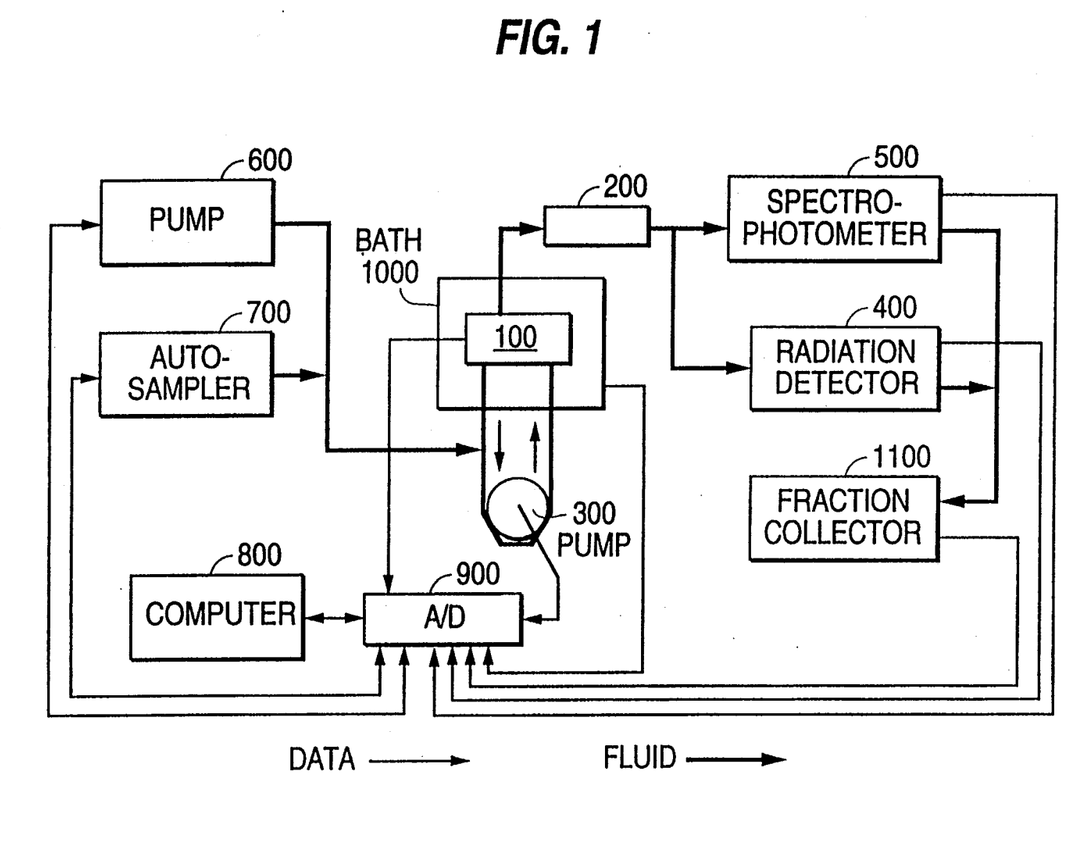
FIG. 1 is a block diagram of a system for use in the continuous, cell-free in vitro synthesis of peptides or peptide-MHC complexes.
Figure 2A:
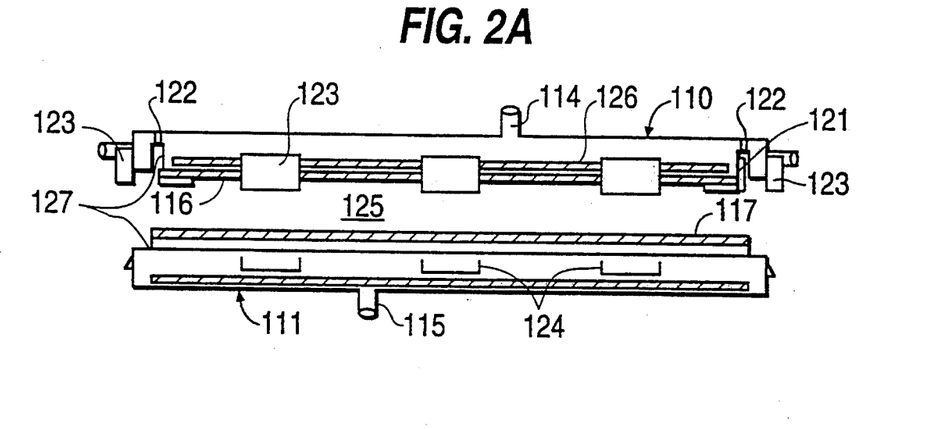
FIG. 2A is an exploded longitudinal cross-section.
Figure 2B:
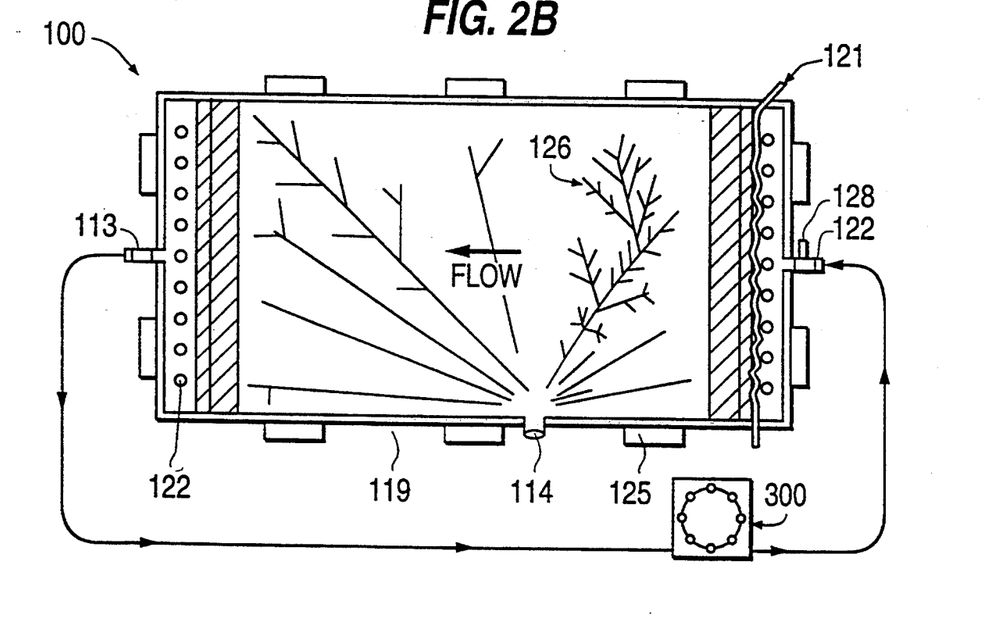
FIG. 2B is a cutaway view showing the grooves on the inside of the housing through which the eluate flows.
Figure 2C:
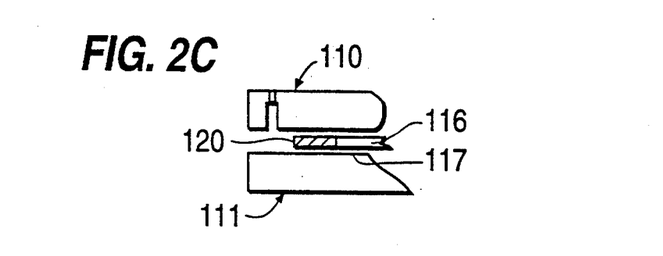
FIG. 2C is a detail showing the arrangement of the membranes and the porous spacer.

An in vitro system for continuous cell-free synthesis of a peptide on a preparative scale in accordance with the present invention is shown in FIG. 1. A key feature of this system is bioreactor flow cell 100. A commercially-available device useful as bioreactor flow cell 100 is manufactured by FILTRON TM, under the name MINI ULTRASETTE TM. However, a novel and more preferred bioreactor flow cell in accordance with the present invention is shown in detail in FIGS. 2A, 2B and 2C. Unlike commercially-available devices, the novel bioreactor flow cell according to FIG. 2 is reusable. It also has several features not available in commercial devices.

FIG. 2B is longitudinal cross-section of bioreactor flow cell 100. Bioreactor flow cell 100 has a two-part outer housing, comprising upper housing 110 and lower housing 111, which define chamber 127. The two-part housing is made of a hard, plastic material. Upper housing 110 and lower housing 111 are fastened together with clamps 123 and latches 124. Clamps 123 and latches 124 are preferably made of steel. O-ring 119 is positioned between upper housing 110 and lower housing 111, to ensure a tight seal between the two housings.

Ultrafiltration membranes 116, 117 are contained in upper housing 110 and lower housing 111, respectively. Porous spacer 120 is positioned between membranes 116, 117 at each end of the chamber to maintain space 125 between the membranes. Porous spacer 120 is preferably made of POREX TM. The pore size of membranes 116, 117 is of size such that a cell lysate is restricted to space 125, while peptides produced by the lysate can flow through membranes 116, 117. Suitable membranes are manufactured by FILTRON TM available under the name OMEGA TM. A useful membrane size is in the range of 70–100 okilodaltons (kD).

Inlet 112 is at one end of the housing and outlet 113 is at the other end of the housing. A reaction mixture enters space 125 through inlet 112 and exits space 125 through outlet 113. Both inlet 112 and outlet 113 have HPLC fittings. Inlet 112 has a T-fitting 128 to permit introduction of additional solution to the chamber during operation of the bioreactor flow cell. After a reaction mixture flows into the housing, the flow is distributed at right angles to the longitudinal axis of the bioreactor flow cell. The reaction mixture then flows along the longitudinal axis of the cell, in space 125 between the membranes. The reaction mixture is circulated through space 125 in bioreactor flow cell 100 by peristaltic pump 300 (GILSON TM M312), which induces a laminar flow. This laminar flow mixes the reaction mixture without introducing air into the mixture, as is the case in systems using a magnetic stir bar. Bioreactor flow cell 100 is contained in a precision, electronically controlled water bath 1000, for example, NESLAB TM RTE110.

Products produced in bioreactor flow cell 100 flow through membranes 116, 117. Both upper housing 110 and lower housing 111 have on their inner surface a pattern of grooves 126, shown in FIG. 2B, in which eluate is collected. Groove pattern 126 is a leaf-like fractal pattern with interspersed, fine stippling to allow passage of eluate between the membranes and the outer housing. Collected eluate exits bioreactor flow cell 100 through at least one eluate port. In a first embodiment, two separate eluate ports are used. A first eluate port 114 is contained in upper housing 110 and a second eluate port 115 is contained in bottom housing 111. This embodiment is particularly useful for research and/or process optimization. By using membranes having different cutoffs for molecular weight in each of upper housing 110 and lower housing 111, membrane cutoff size can be readily optimized. During production, when identical membranes are used in both upper housing 110 and lower housing 111, eluate ports 114 and 115 can be externally connected with tubing to produce a single eluate for collection and analysis. In an alternative embodiment, the pattern of grooves 126 are connected within the housing to exit at a single eluate port.

Small holes 122, approximately one-eighth in diameter, can be associated with one or both of inlet 112 and outlet 113, in order to attach one or more sensors to monitor various properties of the reaction mixture. For example, pH, ionic strength and ion selective sensors, as well as a thermocouple or thermistor, can be used to monitor the solution. For the most precise control, a given property is monitored at both inlet 112 and outlet 113, so that variations in the property as the reaction mixture passes through the flow cell can be determined. Alternatively, a property may be monitored at only one of inlet 112 and outlet 113.

Bioreactor flow cell 100 also has thermal transfer coil 121 associated with inlet 112, in order to vary the temperature of the reaction mixture. In an alternative embodiment, thermal transfer coils are associated with both inlet 112 and outlet 113. This embodiment is used when it is desired to oscillate the reaction mixture flow in bioreactor flow cell 100.

A characteristic feature of bioreactor flow cell 100 is a high ratio of surface area of the membranes to the volume of chamber 127. A ratio of surface area to volume is not a unitless quantity, but is expressed in inverse units (units$^{-1}$). In accordance with the present invention, this ratio is at least about 5 units$^{-1}$. A ratio of greater than about 15 units$^{-1}$, particularly more than about 20 units$^{-1}$, is preferred For example, a total membrane area of 50 cm$^2$ and a chamber volume of 2.5 cm$^3$ (a ratio of 20 units$^{-1}$) has been found to give excellent results.

The high ratio of membrane surface area to the chamber volume permits high perfusion rates through the system with lower flux rate per membrane area. The high ratio also may have a field flow fractionation effect. Additionally, it is believed that this high ratio of surface area to chamber volume provides improved results because it results in a small diffusion path length for the molecules. The diffusion distance to the membrane at any point in the reaction chamber is less than about 1 mm.

The high membrane-surface-area-to-chamber-volume allows use of a relatively low chamber running pressure of less than about 40 psi at high flow flux rates of 6 ml/hr or greater. This in turn permits the use of thinner tubing and reactor walls, leading to better thermal transfer between the reaction chamber and the water bath.

While the essential element of the in vitro system for preparative-scale, continuous, cell-free synthesis in accordance with the present invention is bioreactor flow cell 100, this cell can be used in concert with a variety of other components to provide a more refined system. An important refinement is countercurrent flow dialysis cell 200, through which eluate from bioreactor flow cell 100 flows in order to remove radioactively-labelled or fluorescently-labelled amino acid that is not incorporated into the peptide being synthesized by the system. This eliminates the high level of background counts that would arise from unincorporated labelled amino acid, permitting an extremely accurate determination of the level of protein-bound radioactivity or fluorescence.

Figure 3A:
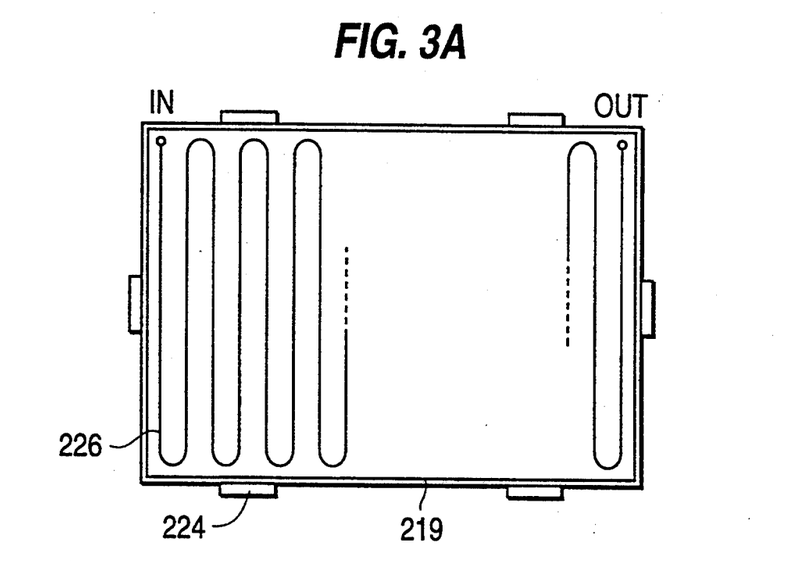
FIG. 3A is a cutaway view showing the grooves through which either eluate or rinse solution flows.
Figure 3B:
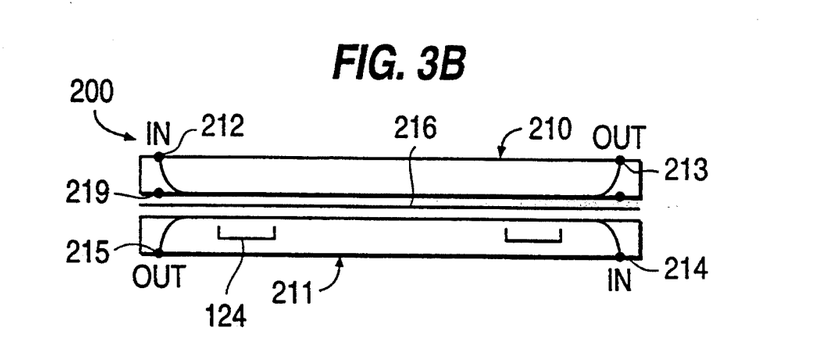
FIG. 3B is a longitudinal cross-section.
Figure 3C:
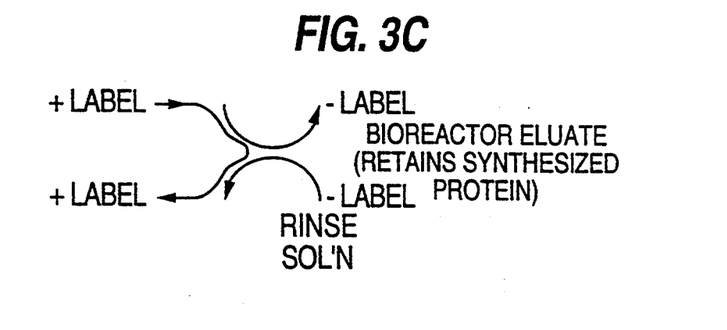
FIG. 3C is a detail explaining the countercurrent mechanism.

Countercurrent flow dialysis cell 200 is shown in FIGS. 3A, 3B and 3C. Like bioreactor flow cell 100, it has a two-part outer housing, comprising upper housing 210 and lower housing 211. The two-part housing is made of a hard, plastic material. Upper housing 210 and lower housing 211 are fastened together with clamps 223 and latches 224. Clamps 223 and latches 224 are preferably made of steel. O-ring 219 is positioned between upper housing 210 and lower housing 211, to ensure a tight seal between the two housings.

Both upper housing 210 and lower housing 211 have on their inner surface identical grooved pattern 226. In order to provide a large exchange surface area in a small space, grooved pattern 226 is preferably a serpentine configuration, as shown in FIG. 3A. A useful configuration uses a groove that is approximately 1 mm wide and deep and at least one-half meter long. A rinse solution flows through grooved pattern 226 in upper housing 210 and bioreactor eluate flows through grooved pattern 226 in lower housing 211. Rinse solution flows into dialysis cell 200 through inlet 212 in upper housing 210 and out through outlet 213 in upper housing 210. Bioreactor eluate flows into dialysis cell 200 through inlet 214 in lower housing 211 and out through outlet 215 in lower housing 211. Rinse solution inlet 212 is positioned adjacent bioreactor eluate outlet 215 and bioreactor eluate inlet 214 is positioned adjacent rinse solution outlet 213.

Dialysis membrane 216 is positioned between upper housing 210 and lower housing 211. The molecular weight cutoff for this membrane must be such that it retains the peptide being synthesized, while allowing the amino acids to pass. A membrane having a cutoff as close as possible to but less than the molecular weight of the protein is preferred. For example, when synthesizing globin, which has a MW of about 14 kD, the cutoff for the dialysis membrane can be 10 kD or lower.

As bioreactor eluate passes through dialysis cell 200, small molecules, including the radioactively-labelled amino acids, are free to pass through dialysis membrane 210 in response to the concentration gradient which exists between the bioreactor eluate and the rinse solution, while peptide is retained in the bioreactor eluate.

The concentration of radioactively-labelled amino acids decreases in the bioreactor eluate between inlet 214 and outlet 215 while their concentration increases in the rinse solution between inlet 212 and 213. This countercurrent mechanism of exchange is shown in FIG. 3C. As bioreactor eluate enters at inlet 214, the concentration of radioactively-labelled amino acids is high. Thus, even though the concentration of radioactively-labelled amino acids in the rinse solution is high at this point, a concentration gradient still exists, and labelled amino acids will pass through dialysis membrane 226 and into the rinse solution. As bioreactor eluate approaches outlet 215, the concentration of labelled amino acid is low, but since it is now in contact with fresh rinse solution, a gradient still exists, and labelled amino acids will pass through dialysis membrane 226 and into the rinse solution.

After exiting countercurrent flow dialysis flow cell 200, the bioreactor eluate goes to radiochromatography detector 400 for detection of peptide-bound radioactivity. Any detector typically used in high performance chromatography is suitable, for example, the RADIOMATIC ™ A500. The bioreactor eluate can also be sent to optical absorbance spectrophotometer 500, for measurement of protein concentration, or another analysis device, such as a mass spectrometer, for measuring protein product or lysate component mass. The absorbance profile also can provide an estimate of the general composition of the peptide produced. These two measurements are used during process optimization, and may be omitted once a process has been optimized. Fractions are collected in fraction collector 1100.

The system according to the present invention may include components to vary the composition of the feed solution component of the reaction mixture flowing through bioreactor flow cell 100. These components are particularly useful for research and/or process optimization.

One example of such component is pump 600, which is capable of dispensing a number of stock solutions. For example, a quaternary pump normally used for high performance liquid chromatography, such as the HEWLETT PACKARD TM 1050 series quaternary pump can dispense up to four different solutions. An infinite variety of feed solution compositions is possible by mixing various amounts of the four stock solutions.

Another example of a component which can be used to vary the composition of the feed solution is autosampler 700. An example of autosampler 700 is the HEWLETT PACKARD TM 1050 series autosampler normally used for high performance liquid chromatography. Autosampler 700 allows for injection into the feed solution of various ingredients. Autosampler 700 can be used to replace specific ingredients lost during operation of the process, such as essential enzymes, elongation factors, mRNA or tRNA. Alternatively, autosampler 700 can be used to inject a readily measured ingredient, for example, a radiolabelled amino acid, an mRNA or an elongation factor, for pulse-chase studies.

The entire apparatus is conveniently placed under control of computer 800. A commercially-available program such as Visual Engineering Environment TM can be used to control parameters such as temperature, flow rate and feed solution composition in order to optimize a particular process. Computer 800 can communicate directly with digital components, such as the Hewlett Packard autosampler and quaternary pump. For analog components, such as peristaltic pump 300, analog-to-digital converter 900 is used between the computer and the component.

The apparatus according to the present invention can be used for the continuous, cell-free in vitro synthesis of a peptide or a peptide-MHC complex. A mixture of a cell lysate and a feed buffer containing an mRNA construct encoding a peptide are circulated through the bioreactor flow cell. Both endogenous mRNA as well as exogenous mRNA constructs can be used to manufacture peptides. The peptides encoded by the mRNA construct are eluted through the membranes of the bioreactor cell and collected. A summary of techniques for in vitro synthesis of proteins is provided by A. Spirin in THE RIBOSOME (Hill, W. E., et al. 1990) ISGN 1-55581-020-9, Chapter 2, the contents of which are incorporated herein by reference.

The cell lysate for synthesis of the peptides can be a lysate of either prokaryotic or eukaryotic cells. Commonly used lysates include *E. coli* lysates, wheat germ lysates and rabbit reticulocyte lysate. The cell lysate provides the ribosomes and most other factors necessary for peptide synthesis. In a preferred embodiment, a lysate of rabbit reticulocytes is used. When used to test a gene therapy, the lysate selected is that of cells that will become the target of the gene. For example, endothelial cell lysate may be used to test efficacy of translation of a gene for plasminogen activator.

A feed buffer provides the amino acids from which the peptide is formed. One of the amino acids can be radioactively labelled in order to determine the progress of the reaction. The feed buffer also provides other ingredients essential to maintain the cell lysate in an active state. These ingredients include, inter alia, $Mg^{2+}$, ATP, GTP, spermidine, folate and buffers. The feed buffer is not filtered, and lyophilized ATP and GTP also are added immediately prior to use.

More particularly, reticulocyte lysate that either has or has not been treated with micrococcal nuclease (PROMEGA TM) is thawed and supplemented with hemin, ribonuclease inhibitor (RNAsin), tRNA (calf liver, courtesy of L. Kohlstadt and T. Steitz, Yale University), creatine kinase, magnesium acetate and dithiothreitol. This solution is mixed with feed solution and infused into the bioreactor chamber. One milliliter of reticulocyte lysate is mixed with 2 milliliters of feed solution to produce a total of 3 milliliters, the total volume of the bioreactor including the tubing completing the flow circuit. The volume is constant and the circuit is free of any gas phase.

Feed solution is then infused at a rate that provides at least 6 volume exchanges per hour, although higher flow rates may be used. For example, when 1 ml of lysate is used the flow rate is least about 6 ml/hr. Since the system is a closed loop, the rate of addition of feed solution equals the rate of production of eluate. The system can be operated continuously, until the desired quantity of peptide is synthesized. The water bath temperature is set to the temperature optimum for the cells used, typically between about 27° and 30° C. It has been discovered the peristaltic pump significantly cools the circulating reaction mixture, at least during the first few hours of operation. Thus, while the water bath may be at 30° C., the temperature of reaction mixture as it emerges from the bioreactor is about 27.6° C. The peristaltic pump is set at about 25 to 45 cc/min, preferably about 35 cc/min, to circulate the reaction mixture through the bioreactor and mix with the lysate which is circulated through the chamber by peristaltic pump at 35 cc/min plus or minus 10.

Aliquots of eluted fractions are analyzed qualitatively by SDS-PAGE (8–25% gradient, PHAST System, PHARMACIATM TM). Yield is calculated from TCA-precipitable cpm/100 $\mu$l of eluate and is confirmed by HPLC radiochromatography (A525 and Analysis software, RADIOMATICTM TM).

According to the present invention, the mixture of lysate and feed solution can be used to synthesize protein from endogenous mRNA. When reticulocyte lysate is used the endogenous protein produced is globin.

The synthesis of globin by reticulocyte lysate can be used as a benchmark against which synthesis of other polypeptides encoded by exogenous DNAs in the reticulocyte lysate system can be judged. Reticulocytes are best at producing globin. The synthesis rate for endogenous globin in reticulocyte lysate therefore is a maximum synthesis rate against which other syntheses can be assessed.

To synthesize globin, reticulocyte lysate containing the mRNA construct for globin and feed buffer containing the mRNA construct for globin are placed in the bioreactor flow cell. The reaction mixture is circulated through the bioreactor flow cell, and globin synthesized by the cell lysate passes through the membranes and is eluted as product. The globin is eluted in substantially pure form. Extremely high expression rates have been obtained with the system according to the present invention. As much as 17 mg globin/ml of lysate has been obtained in six hours.

The system also can be employed, using exogenous mRNA, to make other peptides. Messenger RNA constructs are made from cDNA in vitro using standard methods described, for example, by Maniatis, T., E. F. Fritsch, and J. Sambrook [1982] MOLECULAR CLONING: A LABORATORY MANUAL (Cold Spring Harbor Laboratory, Cold Spring Harbor, NY), the contents of which are incorporated herein by reference. By using PCR-derived gene product to produce mRNA and then using this mRNA to produce protein, the need for plasmid DNA and cloning techniques is obviated, a distinct advantage of method according to the present invention.

From cDNA, an mRNA construct is made in which the 5' and 3' untranslated domains for the endogenous protein flank the gene of interest, using an RNA polymerase such as T7 or SP6. In the reticulocyte lysate system, the 5' and 3' untranslated domains for $\alpha$ and $\beta$-globin flank the gene of interest, while in the *E. coli* system, the 5' and 3' untranslated domains for thioredoxin flank the gene of interest. The mRNA produced then is used to manufacture the peptide corresponding to the gene of interest. Messenger RNA contracts can be made in advance and stored in ethanol. Since ethanol can inhibit translation, it is preferred that it be removed by washing before the construct is added to the feed buffer.

When using the reticulocyte lysate system, the only peptide contaminant is globin. Since globin is highly water soluble, it is easy to separate from the peptide of interest, making this system of particular interest.

The system according to the invention also can be used in coupled transcription/translation studies.

It is apparent that the great control of variables afforded by the system provides the ability to study both translation and transcription control in detail. Pulse-chase studies enable the kinetics of RNA transcription or mRNA translation to be studied. The system also can be used to study various gene therapy strategies involving both the production of a protein and the inhibition of protein translation.

A significant utility of the present system is in the synthesis of peptide-MHC complexes. To synthesize a peptide-MHC complex, it is preferable first separately to synthesize the peptide to be incorporated into peptide-MHC complex by conventional techniques. This peptide is added to the feed buffer which is then added to the reticulocyte lysate, in an amount of 100 micromoles or more, to form the reaction mixture. mRNA constructs for MHC Class I molecule or for both chains of MHC Class II are used to synthesize the MHC molecule in vitro. The mRNA constructs preferably are modified with respect to the native gene to eliminate the transmembrane hydrophobic portion of the molecule.

When MHC Class I molecules are being synthesized, B2 microglobulin must also be provided. This can either be achieved by adding an mRNA construct for B2 microglobulin to the reaction mixture, or preferably by separately obtaining B2 microglobulin and adding it to the feed buffer. B2 microglobulin is readily obtained from blood. By adding both the peptide and the B2 microglobulin to the feed buffer, the entire synthetic machinery is directed completely to the synthesis of MHC molecules.

MHC molecules fold into a structure having a groove which binds a peptide and presents it to T-cells. The bound peptides are small. Class I molecules primarily bind endogenous peptide fragments of viral proteins having about 8 or 9 amino acids, while Class II molecules primarily bind exogenous peptide fragments from bacteria having about 7 to 12 amino acids. Folding of the MHC molecule and binding of the peptide is generally a function of microsomes, which may be added to the reaction mixture for the formation of peptide-MHC complexes. Alternatively, passage of the peptides and MHC molecules through the ultrafiltration membrane may provide the conditions necessary for folding and binding.

The present invention provides peptide-MHC complexes having a homogeneous peptide content. This, coupled with the ability to synthesize relatively large quantities of peptide-MHC complexes, makes this system an excellent tool for vaccine production and for immunologic and biophysical studies.

The following examples further explain, but do not limit, the present invention.

EXAMPLE 1. PREPARATION OF FEED BUFFER

To make one liter of feed solution, 800 ml of distilled, deionized, UV-treated (nuclease-free) ultrapure water is added to a one-liter polypropylene tripour container. Ultrapure HEPES HCl (25 mmoles) and ultrapure potassium acetate (150 mmoles) are dissolved in the water. The pH is adjusted to 7.35 with NaOH while stirring with a magnetic stir bar.

After the pH adjustment, 0.6 mmoles of spermidine is dissolved, followed by 1 mmole of dithiothreitol, 0.5 mmoles of magnesium acetate, 1 mmole ATP, 0.2 mmole GTP, and 10 mmole creatine phosphate. Then 100 $\mu$moles of each essential amino acid except leucine and methionine are simultaneously added. The amino acids are in lyophilized form. It is essential to ascertain that the amino acids have dissolved fully. This usually requires about one-half to one hour.

After the amino acids have dissolved, 5 mg of folate is added. Again, full dissolution is critical. After the folate has fully dissolved, the pH is again adjusted to 7.4, using NaOH, and the volume is brought to one liter, using the ultrapure wetter described above. The feed buffer is not filtered, but is aliquoted into sterile 50 ml conical polypropylene tubes and immediately frozen at $-80°$ C.

The feed buffer is thawed as needed, initially at room temperature and then, when only a small amount of the solution is still frozen, on ice. Immediately prior to use, 20 microliters of 1 millimolar hemin prepared as described in the PROMEGA TM reticulocyte lysate manual (1993) is added to 50 ml of feed buffer. Sodium azide (0.01% w/w) is added to the 50 ml aliquot, and then lyophilized ATP (0.05 mmoles), GTP (0.01 mmoles) and creatine phosphate (0.05 mmoles are added to each 50 ml aliquot of feed solution.

To one ml of the 50 ml aliquot is added 100 $\mu$moles of lyophilized methionine. The methionine is dissolved by raising the temperature of the solution to approximately 35° C. This amino acid is added immediately before use because of its sensitivity to oxidation. Then 25 $\mu$l of the methionine solution is added to each 50 ml aliquot of feed solution to make the solution 50 $\mu$molar with respect to methionine.

To another one ml of the 50 ml aliquot 100 $\mu$moles of leucine is added using the same technique as for the methionine. Then 100 $\mu$l of the leucine solution is added to each 50 ml aliquot of feed solution to make the solution 200 $\mu$molar with respect to leucine.

One MCl of translation-grade $S^{35}$-methionine (specific activity approximately 1000 Ci/mmole) in 50 $\mu$l is added to the 50 ml aliquot immediately before use of the feed buffer in the system. The radiolabel may be omitted in a production run for which the optimum conditions already have been determined.

EXAMPLE 2. PREPARATION OF LYSATE

Reticulocyte lysate is obtained from PROMEGA ™. The lysate is nuclease-treated unless it is being used for globin synthesis from endogenous mRNA. Frozen lysate is thawed carefully on ice and maintained at 4° C. during subsequent preparation. Twenty μl (40,000 units/ml) of recombinant ribonuclease inhibitor (PROMEGA ™) is added. The solution is agitated gently by rolling the container between the palms.

To this solution is added the following, in each case with gentle agitation before the next addition:
   8 μl of 0.25 mmoles dithiothreitol
   5 μl of 10 mg/ml creatine phosphokinase (in 20 mM tris-HCl and 50% glycerol)
   5 μl of 0.2 M magnesium acetate solution
   12 μl of 4.3 mg/ml calf-liver tRNA

EXAMPLE 3. SYNTHESIS OF ENDOGENOUS DNA

One ml untreated lysate prepared according to Example 2 is placed in a 3 ml syringe with 2 ml of feed buffer prepared according to Example 1. The contents of the syringe is injected into the bioreactor flow cell.

Additional feed buffer is injected into the closed loop of the bioreactor flow cell at a flow rate of 6 ml/hr. A synthesis rate of 17 mg/ml of lysate/6 hrs) is achieved as measured by $S^{35}$ methionine incorporation on both TCA precipitation and on HPLC radiochromatography. The radioactivity is seen travelling exclusively with the globin band.

EXAMPLE 4. SYNTHESIS OF EXOGENOUS DNA

From cDNA, an mRNA construct is made in which the 5' and 3' untranslated domains for the globin flank a gene of interest, using an RNA polymerase such as T7 or SP6. One ml nuclease-treated lysate prepared according to Example 2 and 3 μg of the mRNA construct are placed in a 3 ml syringe with 2 ml of feed buffer prepared according to Example 1. The contents of the syringe is injected in the bioreactor flow cell.

Additional feed buffer is injected into the closed loop of the bioreactor flow cell at a flow rate of 6 ml/hr. Synthesis rate is measured by $S^{35}$ methionine incorporation on both TCA precipitation and on HPLC radiochromatography. Globin is removed from the desired peptide based on a difference in solubility.

EXAMPLE 5. SYNTHESIS OF PEPTIDE-MHC COMPLEXES

The peptide to be incorporated into peptide-MHC complex is synthesized by conventional techniques. An optimum amount of this peptide then is added to the feed buffer prepared according to Example 1. This is then added to reticulocyte lysate to form the reaction mixture. Messenger RNA constructs for MHC Class I molecule that have been modified to eliminate the transmembrane hydrophobic portion of the molecule are added, to synthesize the MHC molecule in vitro. B2 microglobulin, isolated according to standard techniques, is added to the reaction mixture.

Additional feed buffer is injected into the closed loop of the bioreactor flow cell at a flow rate of 6 ml/hr. Synthesis rate is measured by $S^{35}$-methionine incorporation using both TCA precipitation and HPLC radiochromatography assays. Globin is removed from the peptide-MHC complex by virtue of a difference in solubility and/or by standard chromatographic techniques, including immunoaffinity chromatography.

While the invention has been described in detail with respect to particular preferred embodiments, it should be understood that such description is presented by way of illustration and not limitation. Many changes and modifications within the scope of the present invention may be made without departing from the spirit thereof, and the invention includes all such modifications.

What is claimed is:

1. A bioreactor flow cell comprising:
   a chamber,
   a pair of substantially parallel membranes positioned within the chamber to define therebetween a space, a ratio of total surface area for said pair of membranes to the volume of the chamber is at least 5 units$^{-1}$,
   an inlet at one end of the chamber for admitting a solution into the space between the membranes and an outlet at the other end of the chamber for removing the solution from the space between the membranes,
   thermal transfer means associated with at least one of the inlet and the outlet for affecting the temperature of a solution flowing into the bioreactor flow cell, and
   an eluate port in communication with the chamber.

2. A bioreactor flow cell as recited in claim 1, wherein the ratio of total surface area of the pair of membranes to the volume of the chamber is at least 15 units$^{-1}$.

3. A bioreactor flow cell comprising:
   a chamber,
   a pair of substantially parallel membranes positioned within the chamber to define therebetween a space, a ratio of total surface area for said pair of membranes to the volume of the chamber is at least 5 units$^{-1}$,
   an inlet at one end of the chamber for admitting a solution into the space between the membranes and an outlet at the other end of the chamber for removing the solution from the space between the membranes,
   means associated with at least one of the inlet and the outlet for attaching at least one sensor to monitor a property of a solution flowing through the bioreactor flow cell, and
   an eluate port in communication with the chamber.

4. A bioreactor flow cell as recited in claim 3, further comprising thermal transfer means associated with at least one of the inlet and the outlet for affecting the temperature of a solution flowing through the bioreactor flow cell.

5. A bioreactor flow cell as recited in claim 3, further comprising thermal transfer means associated with both the inlet and the outlet for affecting the temperature of a solution flowing through the bioreactor flow cell.

6. A bioreactor flow cell as recited in claim 3, wherein the ratio of total surface area of the pair of membranes to the volume of the chamber is at least 15 units$^{-1}$.

7. A bioreactor flow cell as recited in claim 3, further comprising spacer means for maintaining a space between the pair of membranes.

8. A bioreactor flow cell as recited in claim 7, wherein the spacer means is made of a porous plastic.

9. A bioreactor flow cell as recited in claim 7, wherein the chamber comprises separable top and bottom halves that allow the membranes to be changed.

10. A bioreactor flow cell as recited in claim 3, comprising means associated with both the inlet and the outlet for attaching at least one sensor to monitor a property of a solution flowing through the bioreactor flow cell.

11. A bioreactor flow cell as recited in claim 10, comprising means associated with both the inlet and the outlet for attaching a plurality of sensors to monitor different properties of the solution flowing through the bioreactor flow cell.

12. A bioreactor flow cell as recited in claim 11, comprising a sensor in each of the inlet and the outlet to monitor ionic strength of the solution.

13. A bioreactor flow cell as recited in claim 10, further comprising thermal transfer means associated with at least one of the inlet and the outlet for affecting the temperature of a solution flowing through the bioreactor flow cell.

14. An in vitro system for continuous cell-free synthesis of a peptide on a preparative scale, comprising:
a bioreactor cell as claimed in claim 3, and
means for circulating a feed buffer containing amino acids and an mRNA construct encoding a peptide through the bioreactor cell.

15. A system as claimed in claim 14, wherein the bioreactor flow cell further comprises thermal transfer means associated with at least one of the inlet and the outlet for affecting the temperature of a solution flowing through the bioreactor flow cell.

16. A system as claimed in claim 15, additionally comprising a countercurrent flow dialysis cell positioned after said bioreactor flow cell, through which product from the bioreactor flow cell is passed, said dialysis cell comprising an upper housing, a lower housing and a dialysis membrane positioned between the upper and lower housings.

17. A system as claimed in claim 16, additionally comprising means for varying the composition of the solution circulating in the bioreactor flow cell.

18. A system as claimed in claim 17, wherein the means for varying the composition of the solution comprises a pump adapted to pump a plurality of solutions.

19. A system as claimed in claim 17, wherein the means for varying the composition of the solution comprises an autosampler for introducing a known amount of a single ingredient into the solution circulating in the bioreactor flow cell.

20. A system as claimed in claim 17, additionally comprising a radiochromatography detector.

21. A system as claimed in claim 17, additionally comprising an optical absorbance spectrophotometer.

22. A system as claimed in claim 17, additionally comprising a computer for automatically controlling the system.

23. A system as claimed in claim 16, wherein the upper housing and the lower housing have on their inner surfaces a grooved pattern with an inlet and an outlet, the lower housing grooved pattern being a mirror image of the upper housing grooved pattern, with the inlet of the upper housing grooved pattern being adjacent the outlet of the lower housing grooved pattern and the outlet of the upper housing grooved pattern being adjacent the inlet of the lower housing grooved pattern.

* * * * *